United States Patent [19]

Farinas

[11] Patent Number: 5,486,537

[45] Date of Patent: Jan. 23, 1996

[54] TOPICAL ANTI-FUNGAL COMPOSITION FOR SKIN AND KERATINOUS TISSUE

[75] Inventor: Reynaldo G. Farinas, Miami, Fla.

[73] Assignee: Dayton Laboratories, Inc., Miami, Fla.

[21] Appl. No.: 375,705

[22] Filed: Jan. 20, 1995

[51] Int. Cl.[6] .......................... A61K 31/335; A61K 31/34; A61K 31/11; A61K 31/045

[52] U.S. Cl. ........................ 514/462; 514/701; 514/724

[58] Field of Search ................................. 514/462, 701, 514/724

[56] References Cited

PUBLICATIONS

CA 87:51751, Bullerman et al., 1977.
CA 117:1440, Liang, 1991.
CA 117:33729, Uhrova et al., 1990.
CA 105:49083, Kamiya et al., 1986.

Primary Examiner—Kimberly Jordan
Attorney, Agent, or Firm—Watson, Cole, Grindle & Watson

[57] ABSTRACT

An antifungal composition which can be topically applied to skin and keratinous tissue and is active against the fungi *Trichophyton mentagrophytes* and *Candida albicans* includes griseofulvin dissolved in a solvent blend of cinnamic aldehyde and alcohol, particularly isopropanol. Topical antifungal compositions of cinnamic aldehyde in isopropyl alcohol are also provided. Packaged products are provided and include the compositions disposed in sealed containers. A method is also provided for treating keratinous tissue infected with the fungi.

29 Claims, No Drawings

TOPICAL ANTI-FUNGAL COMPOSITION FOR SKIN AND KERATINOUS TISSUE

FIELD OF THE INVENTION

The present invention relates to an antifungal composition which can be applied topically to fingernails and toenails infected with *Trichophyton mentagrophytes* and *Candida albicans*. More specifically, the present invention relates to a compositions of cinnamic aldehyde, griseofulvin and isopropyl alcohol.

BACKGROUND OF THE INVENTION

*Trichophyton mentagrophytes* and *Candida albicans* are the two most common fungi which infect human toenail and fingernail tissue and are responsible for the vast majority of nail infections, medically termed onychomycosis, in the United States. The present inventor knows of no effective topical medication which is currently approved by the FDA and available for the treatment of such fungal infections.

Griseofulvin is a cream powder produced by Penicillium griseofulvum and has the formula $C_{17}H_{17}O_6Cl$. The griseofulvin molecule has a heterocyclic nucleus and a spyran ring junction. It is widely used as an oral antimycotic for many disease conditions. It is effective against *Trichophyton mentagrophytes* but is absorbed slowly after ingestion and thus does not provide high blood serum concentrations. Therefore, lengthy treatment periods are required. Griseofulvin is toxic to the liver and requires medical supervision. As a consequence, griseofulvin is not suitable for over-the-counter use.

Griseofulvin is available in tablet or capsule form by prescription to be orally administered for the treatment of *Trichophyton mentagrophytes*. Unfortunately, it requires a lengthy treatment time of between six months and several years and entails continuous, expensive therapy. Griseofulvin has been considered completely ineffective against fungal infections caused by *Candida albicans*.

Furthermore, griseofulvin is only slightly soluble in water and is poorly absorbed by skin and nail tissue. Previous attempts to provide a non-toxic, effective topical medication of griseofulvin have been unsuccessful. Compositions of griseofulvin dissolved in many aprotic solvents have been unsuccessful because the resultant solutions are toxic or exhibit other properties which severely limit their effectiveness and applicability. For example, two particular aprotic solvents are dimethyl sulfoxide (DMSO) and dimethyl formamide (DMF). DMSO and DMF can be used as solvents for griseofulvin and enable griseofulvin to penetrate skin and keratinous tissue. However, both of these solvents are toxic compounds. In fact, DMSO was generally taken off the market for medicinal use by the U.S. Food and Drug Administration years ago. No other permeation enhancers have been found to be effective in moving griseofulvin into skin and keratinous tissue. Also, none of the known and tested permeation enhancers exhibit any substantial effectiveness against *Candida albicans*.

Cinnamic aldehyde (PhCH:CHCHO, also known as cinnamaldehyde or β-Phenylacrolein) has been considered a popular flavoring agent and aromatic agent. The solubility of cinnamic aldehyde in alcohol is known from Table C-233 of *Handbook of Physics and Chemistry*, 65th ed., from CRC Press (1984–1985). The present inventor presently knows of no previous antimycotic use of cinnamic aldehyde and of no packaged product comprising a sealed container having a solution of cinnamic aldehyde and alcohol therein.

Cinnamic aldehyde is the major ingredient in the natural plant oil—oil of cinnamon—which has been used as a folk remedy for the treatment of painful teeth and gums. It is also used as an itch remedy. Cinnamic aldehyde is on the U.S. Food and Drug Administration's list of agents which are "generally recognized as safe", that is, the GRAS list. Although there are aldehydes with antimicrobial activity, such as the familiar embalming fluids formaldehyde and glutaraldehyde, these latter two are particularly toxic to human tissue and cannot be safely used as medications.

A need therefore exists for a non-toxic antifungal composition which can be topically applied and is effective against infections of both *Trichophyton mentagrophytes* and *Candida albicans*. A need also exists for a topical composition which provides adequate solration of griseofulvin, an enhancement in permeation and penetration of griseofulvin into keratinous tissue, and a stable shelf life.

SUMMARY OF THE INVENTION

The present invention is based upon the discovery that griseofulvin can be dissolved in cinnamic aldehyde to provide a non-toxic composition which can be topically applied and has a stable shelf life. The present invention is also based on the discoveries that the resulting solution, and solutions of cinnamic aldehyde and isopropyl alcohol, are effective as antifungal medicaments against infections of *Trichophyton mentagrophytes* and *Candida albicans*.

In one embodiment, the present invention relates to a solution of cinnamic aldehyde in isopropyl alcohol and a topical composition comprising the solution. In another embodiment, the invention relates to a solution of griseofulvin dissolved in cinnamic aldehyde and a polar solvent such as isopropyl alcohol or ethyl alcohol, and it relates to topically applied compositions comprising the solution. The compositions of griseofulvin, cinnamic aldehyde, and alcohol according to the present invention provide adequate solvation of griseofulvin and enhanced permeation and penetration of griseofulvin into skin and keratinous tissue. In one preferred embodiment, the present invention relates to a composition of griseofulvin dissolved in cinnamic aldehyde and specifically isopropyl alcohol.

Methods of treating skin and keratinous tissue infected with *Trichophyton mentagrophytes* or *Candida albicans*, or both, are also provided according to the invention. According to the methods of the present invention, it has been discovered that cinnamic aldehyde is relatively non-toxic to keratinous tissue such as toenails and fingernails.

DETAILED DESCRIPTION OF THE INVENTION

According to the present invention, it has been discovered that solutions of cinnamic aldehyde in an aprotic solvent such as isopropyl alcohol exhibit effective antifungal activity against both *Trichophyton mentagrophytes* and *Candida albicans*, when topically applied to infected keratinous tissue. In one embodiment, the present invention relates to a topical composition which comprises cinnamic aldehyde, also referred to as cinnamaldehyde, in an aprotic solvent, particularly isopropyl alcohol (IPA) or ethyl alcohol (ethanol).

It has been found desirable to dilute the cinnamic aldehyde because of the strong odor released by its pure form. According to the invention, it is expected that solutions of almost 100% cinnamic aldehyde in IPA or ethanol would be extremely effective against both *Trichophyton mentagro-*

*phytes* and *Candida albicans* infections. More practically, solutions of up to about 50% by volume cinnamic aldehyde and a relatively non-toxic aprotic solvent such as IPA or ethanol are effective, economical, and less odiferous. As little as 1% by volume cinnamic aldehyde in IPA or ethanol is expected to provide at least some effectiveness against *Trichophyton mentagrophytes* and *Candida albicans.*

More particularly, solutions of between 30 and 50% by volume cinnamic aldehyde in such solvents are provided according to the present invention. A solution of 40% by volume cinnamic aldehyde in such solvents is provided according to one embodiment of the present invention. In the Examples shown below, a solution of 40% by volume cinnamic aldehyde in IPA is shown to be extremely effective against both *Trichophyton mentagrophytes* and *Candida albicans* infections, and has a pleasing odor.

According to another embodiment, the antifungal composition of the present invention comprises up to about 20% by weight griseofulvin, at least about 20% by volume cinnamic aldehyde, and an alcohol such as IPA or ethanol. While higher amounts of griseofulvin can be used, it is not expected that more than about 20% by weight could be dissolved by any solution of cinnamic aldehyde and IPA. It would be extremely difficult to dissolve even 10% by weight griseofulvin in a solution of cinnamic aldehyde and IPA. While complete dissolution of the griseofulvin is preferred, compositions containing undissolved amounts of griseofulvin are also considered within the scope of the present invention.

According to one particular embodiment of the invention, up to about 10% by weight griseofulvin is present in a composition which also contains at least 20% by volume cinnamic aldehyde and a nontoxic aprotic solvent such as IPA or ethanol. Compositions containing about 0.1 and about 4% by weight griseofulvin are preferred because at such low concentrations the griseofulvin can be completely dissolved and the resultant compositions are nonetheless extremely effective against both *Trichophyton mentagrophytes* and *Candida albicans.*

For compositions containing between about 0.1 and 4% by weight griseofulvin, the amount of cinnamic aldehyde used is preferably in the range of about 20 to about 50% by volume. Cinnamic aldehyde concentrations of between 30 and 40% by volume are particularly preferred for compositions containing about 2% by weight griseofulvin. Compositions containing up to about 20% by weight griseofulvin and the remainder cinnamic aldehyde are also considered within the scope of the present invention. However, it is believed that if no IPA or ethanol is used in the composition, only very small amounts of griseofulvin will dissolve in the otherwise pure cinnamic aldehyde. Also, due to the intense odor of cinnamic aldehyde, if no alcohol solvent is used the odor of the composition is so strong that it is displeasing. Also, cinnamic aldehyde has a thick viscosity making it difficult to apply at high concentrations.

According to another embodiment of the invention, compositions are provided which consist essentially of griseofulvin, cinnamic aldehyde and an alcohol selected from IPA and ethanol. In yet another embodiment, the present invention relates to compositions consisting essentially of cinnamic aldehyde and either IPA or ethanol.

Due to the expense and greater regulation of ethanol, IPA is the preferred alcohol solvent, although both provide similar properties to the resultant composition. The alcohol provides the compositions with many advantageous properties. The alcohol helps dissolve the griseofulvin and acts as a diluent to decrease the viscosity of cinnamic aldehyde or the combined griseofulvin and cinnamic aldehyde. The decreased viscosity enables a more flowable topical composition which can be easily applied by a brush-on applicator, cotton swab or eye dropper, for example. The alcohol also dilutes the odor of the cinnamic aldehyde to provide a less displeasing aroma.

The alcohol also acts as a polar component of the solvent phase. This contributes to the sum of the antifungal effects of both cinnamic aldehyde alone and a solution of griseofulvin and cinnamic aldehyde. The alcohol also exerts a local cleaning and degreasing action during application of the antifungal composition, thus allowing better contact with the surface of the skin or keratinous tissue being treated.

The compositions of the present invention have shown good stability when stored in an amber glass bottle at ambient storage conditions. Compositions comprising 2% by weight griseofulvin, between 20 and 50% by volume cinnamic aldehyde, and the remainder alcohol have been found to be stable in an amber glass bottle at ambient storage conditions for at least one year. Accelerated stability studies indicate that such compositions would be stable for two years or more. Such stability is considered somewhat surprising given the volatility of both cinnamic aldehyde and isopropanol.

Products of the present invention include sealed containers having therein solutions, compositions and mixtures of cinnamic aldehyde, and IPA or ethanol, with and without griseofulvin. A cream or lotion base can also be blended with the compositions of the present invention to form other topically applicable antifungal medicaments.

The invention may be more fully understood with reference to the examples which follow. The examples are provided for the purpose of showing the relative effectiveness of the present compositions when compared to other agents and formulations. The present invention is not to be considered limited to the exemplary embodiments shown below.

EXAMPLES

The antifungal activity of some compositions according to the present invention were evaluated and compared to the activity of several other related aldehydes and agents.

The activity of the various compositions was compared by conducting of inhibition zone tests. A petri dish containing an agar medium is inoculated in the surface of the medium with the fungi *Candida albicans* or *Trichophyton mentagrophytes*. A small filter paper disc, six millimeters in diameter, was soaked in an agent or formulation to be tested until the disc became impregnated. The disc was then allowed to substantially dry and placed on the agar in the center of the petri dish. The average distance away from the disk in which the growth of fungus was inhibited is referred to as the zone of inhibition, and is measured in millimeters. A larger zone of inhibition indicates a greater antifungal activity and a smaller zone of inhibition indicates a lesser antifungal activity. When the growth of fungus is inhibited across the entire surface of the agar medium, the zone of inhibition is determined to be greater than or equal to the maximum measurable zone in the dish. For example, where the zone of inhibition is indicated as greater than or equal to 60 mm, the maximum zone of inhibition in the petri dish tested is 60mm and no fungal growth was observed within that zone.

Table I below shows the zone of inhibition of various agents and compositions and the concentration of those agents and compositions in which the respective test disc was soaked. Table II below shows the effect of the same compositions against *Trichophyton mentagrophytes*. Table III shows a summary of relative effectiveness of two compositions according to the present invention compared to the effectiveness of IPA alone, and griseofulvin in IPA. As can be seen from Table III, the compositions according to the present invention exhibit excellent activity against fungal growth caused by *Trichophyton mentagrophytes* and *Candida albicans*.

The cinnamic aldehyde, and IPA solution showed an extensive range of antifungal activity against both *Candida albicans* and *Trichophyton mentagrophytes*, as shown in Tables I, II and III below. In the tables below, the abbreviation PEG 400 stands for polyethylene glycol 400.

TABLE I

Effectiveness vs. *Candida albicans*.

| Composition or Agent | | Zone of Inhibition (mm)* |
|---|---|---|
| (1) | 20% by volume α-amyl cinnamaldehyde<br>15% by volume oleic acid<br>0.5% by volume citronellal<br>64.5% by volume PEG 400 | 10 |
| (2) | 0% by volume hexyl cinnamaldehyde<br>15% by volume oleic acid<br>0.5% by volume citronellal<br>64.5% by volume PEG 400 | 1 |
| (3) | 10% by volume α-amyl cinnamaldehyde<br>10% by volume hexyl cinnamaldehyde<br>15% by volume oleic acid<br>0.5% by volume citronellal<br>64.5% by volume PEG 400 | 10 |
| (4) | 2% by weight griseofulvin<br>40% by volume cinnamic aldehyde<br>58% by volume IPA | ≧60 |
| (5) | Amyl cinnamaldehyde<br>40% by volume in IPA | 8 |
| (6) | Hexyl cinnamaldehyde<br>40% by volume in IPA | 0 |
| (7) | Cinnamic aldehyde<br>40% by volume in IPA | ≧60 |
| (8) | Oleic acid | 0 |
| (9) | Polyethylene Glycol 400 | 0 |
| (10) | Citronellal | 0 |
| (11) | Griseofulvin<br>2% by weight in IPA | 5 |
| (12) | Blank disc | 0 |

*Zone diameters do not include the 6 mm. disc.

TABLE II

Effectiveness v. *Trichophyton mentagrophytes*.

| Composition or Agent | | Zone of Inhibition (mm)* |
|---|---|---|
| (1) | 20% by volume α-amyl cinnamaldehyde<br>15% by volume oleic acid<br>0.5% by volume citronellal<br>64.5% by volume PEG 400 | ≧60 |
| (2) | 20% by volume hexyl cinnamaldehyde<br>15% by volume oleic acid<br>0.5% by volume citronellal<br>64.5% by volume PEG 400 | 40 |
| (3) | 10% by volume α-amyl cinnamaldehyde<br>10% by volume hexyl cinnamaldehyde<br>15% by volume oleic acid<br>0.5% by volume citronellal<br>64.5% by volume PEG 400 | 45 |
| (4) | 2% by weight griseofulvin<br>40% by volume cinnamic aldehyde<br>58% by volume IPA | ≧60 |

TABLE II-continued

Effectiveness v. *Trichophyton mentagrophytes*.

| Composition or Agent | | Zone of Inhibition (mm)* |
|---|---|---|
| (5) | Amyl cinnamaldehyde<br>40% by volume in IPA | ≧60 |
| (6) | Hexyl cinnamaldehyde<br>40% by volume in IPA | 12 |
| (7) | Cinnamic aldehyde<br>40% by volume in IPA | ≧60 |
| (8) | Oleic acid | 0 |
| (9) | Polyethylene Glycol 400 | 0 |
| (10) | Citronellal | ≧60 |
| (11) | Griseofulvin<br>2% by weight in IPA | 33 |
| (12) | Blank disc | 0 |

*Zone diameters do not include the 6 mm. disc.

TABLE III

| | | Zone of Inhibition (mm)* | |
|---|---|---|---|
| Composition or Agent | | vs. *Trichophyton Mentagrophytes* | vs. *Candida Albicans* |
| (1) | Cinnamic Aldehyde<br>40% by volume in IPA | ≧60 | ≧60 |
| (2) | Isopropyl Alcohol (IPA)<br>anhydrous<br>70% by volume in water | 0<br>0 | 0<br>0 |
| (3) | Griseofulvin<br>2% by weight in IPA | 33 | 0 |
| (4) | Solution of<br>2% by weight griseofulvin<br>40% by volume cinnamic aldehyde<br>58% by volume isopropyl alcohol | 105** | 52 |

*Zone diameters do not include the 6 mm. disc.
**A 150 mm. diameter petri dish was used for this test.

While it appears from Table III as though the solution (4) was less effective against *Candida albicans* than the solution of cinnamic aldehyde in IPA (solution (1)), the present inventor believes that evaporation of the volatiles cinnamic aldehyde and IPA may have accounted for a decrease in activity of solution (4) against *Candida albicans*.

Although the present invention has been described in connection with preferred embodiments, it will be appreciated by those skilled in the art that additions, modifications, substitutions and deletions not specifically described may be made without departing from the spirit and scope of the invention defined in the appended claims.

What is claimed is:

1. In combination, an anti-fungal composition effective against *Trichophyton mentagrophytes* and *Candida albicans*, and a closed container, wherein said composition is disposed within said closed container, said composition comprising a solution of cinnamic aldehyde, up to about 20% by weight griseofulvin, and at least 5% by volume an alcohol selected from the group consisting of isopropanol and ethanol.

2. The combination of claim 1, wherein said alcohol is isopropanol.

3. The combination of claim 1, wherein said composition comprises griseofulvin present in an amount of up to about 10% by weight.

4. The combination of claim 1, wherein said composition comprises between about 20 and about 50% by volume cinnamic aldehyde.

5. The combination of claim 1, wherein said composition comprises between about 30 and about 40% by volume cinnamic aldehyde.

6. The combination of claim 1, wherein said composition comprises griseofulvin present in an amount of up to about 4% by weight.

7. The combination of claim 1, wherein said composition comprises between about 20 and about 50% by volume cinnamic aldehyde, between about 50 and about 80% by volume said alcohol, and further comprises about 2% by weight griseofulvin.

8. The combination of claim 7, wherein said alcohol is isopropanol.

9. An anti-fungal composition effective against *Trichophyton mentagrophytes* and *Candida albicans* consisting essentially of griseofulvin dissolved in cinnamic aldehyde and at least about 5% by volume an alcohol selected from the group consisting of isopropanol and ethanol.

10. An anti-fungal composition as in claim 9, consisting essentially of up to about 20% by weight griseofulvin.

11. An antifungal composition as in claim 9, wherein said alcohol is isopropanol.

12. An antifungal composition as in claim 9, consisting essentially of at least about 5% by volume said alcohol, and griseofulvin present in an amount of up to about 10% by weight.

13. An antifungal composition as in claim 9, consisting essentially of between about 20 and about 50% by volume cinnamic aldehyde.

14. An antifungal composition as in claim 13, consisting essentially of between about 30 and about 40% by volume cinnamic aldehyde.

15. An antifungal composition as in claim 13, consisting essentially of griseofulvin present in an amount of up to about 4% by weight.

16. An antifungal composition as in claim 9, consisting essentially of about 2% by weight griseofulvin, between about 20 and about 50% by volume cinnamic aldehyde, and between about 50 and about 80% by volume said alcohol.

17. An antifungal composition as in claim 16, wherein said alcohol is isopropanol.

18. A method of treating keratinous tissue infected with at least one fungus selected from the group consisting of *Trichophyton mentagrophytes* and *Candida albicans*, comprising the steps of topically applying a composition to said tissue, wherein said composition comprises a solution of cinnamic aldehyde and an alcohol selected from the group consisting of isopropanol and ethanol.

19. A method according to claim 18, wherein said composition further comprises up to about 20% by weight griseofulvin and at least about 5% by volume said alcohol.

20. A method according to claim 19, wherein said composition comprises between about 20 and about 50% by volume cinnamic aldehyde, and between about 50 and about 80% by volume said alcohol, and further comprises about 2% by weight griseofulvin.

21. A method according to claim 20, wherein said alcohol is isopropanol.

22. A method according to claim 18, wherein said alcohol is isopropanol.

23. A method according to claim 18, wherein said composition comprises at least about 5% by volume said alcohol, and further comprises griseofulvin present in an amount of up to about 10% by weight.

24. A method according to claim 18, wherein said composition comprises between about 20 and about 50% by volume cinnamic aldehyde.

25. A method according to claim 18, wherein said composition comprises between about 30 and about 40% by volume cinnamic aldehyde.

26. A method according to claim 18, wherein said composition further comprises griseofulvin present in an amount of up to about 4% by weight.

27. A method according to claim 18, wherein said composition consists essentially of up to about 20% by weight griseofulvin and at least about 5% by volume said alcohol.

28. A method according to claim 18, wherein said composition consists essentially of up to about 4% by weight griseofulvin, between about 20 an about 50% by volume cinnamic aldehyde, and between about 50 and about 80% by volume said alcohol.

29. A method according to claim 18, wherein said composition consists essentially of cinnamic aldehyde and said alcohol.

\* \* \* \* \*